United States Patent [19]

Grasshoff et al.

[11] 3,993,661

[45] Nov. 23, 1976

[54] QUINONE METHIDE PHOTOGRAPHIC REAGENT PRECURSORS

[75] Inventors: J. Michael Grasshoff, Hudson; Lloyd D. Taylor, Lexington, both of Mass.

[73] Assignee: Polaroid Corporation, Cambridge, Mass.

[22] Filed: May 3, 1974

[21] Appl. No.: 466,629

Related U.S. Application Data

[60] Continuation-in-part of Ser. No. 230,064, Feb. 28, 1972, abandoned, which is a division of Ser. No. 99,310, Dec. 17, 1970, Pat. No. 3,698,898.

[52] U.S. Cl. .......... 260/308 D
[51] Int. Cl.² .......... C07D 257/04
[58] Field of Search .......... 260/308 D

[56] References Cited

UNITED STATES PATENTS

| | | | |
|---|---|---|---|
| 3,337,576 | 8/1967 | Buchanan et al. | 260/308 |
| 3,639,417 | 2/1972 | Porter et al. | 260/308 |

*Primary Examiner*—Frederick E. Waddell
*Attorney, Agent, or Firm*—Mart C. Matthews; Philip G. Kiely

[57] ABSTRACT

Novel compounds are disclosed which release a photographic reagent in the presence of alkali and are therefore useful in photographic products and processes. The compounds may be defined as quinone- or naphthoquinonemethide precursors containing a mercapto-azole or azine photographic reagent moiety.

9 Claims, No Drawings

QUINONE METHIDE PHOTOGRAPHIC REAGENT PRECURSORS

CROSS-REFERENCE TO RELATED APPLICATIONS

This application is a continuation-in-part of our copending application Ser. No. 230,064, filed Feb. 28, 1972 and now abandoned, which in turn was a divisional of application Ser. No. 99,310, filed Dec. 17, 1970 and now U.S. Pat. No. 3,698,898, issued Oct. 17, 1972.

BACKGROUND OF THE INVENTION

1. This invention relates to chemistry and, more specifically, to novel compounds per se.

2. Description of the Prior Art

In various photographic systems for forming images, whether in black-and-white or in color, it is often desirable to include in the photographic film unit one or more of the various photographic reagents required for development and/or to enhance image quality. This practice extends to both conventional systems for forming negative images and to the various systems such as diffusion transfer, wherein a positive image in silver or in color is obtained.

In many instances, the photographic reagent may be contained initially in either the processing composition applied for development and image formation or in the film unit, the latter being preferred to reduce and hence simplify the number of ingredients required in the processing composition.

In other instances, the particular photographic reagent desired is not sufficiently stable in alkali to provide the requisite shelf life for the processing composition or the reagent is incompatible and/or reactable with another reagent of the composition and hence must be contained initially in the film unit.

In still other instances, the reagent must be provided at some particular time in the development process, which requires that it be contained in a specified layer or in specified proximity to another layer in the film unit.

In all of the foregoing instances it is desirable that the reagent be contained in the desired layer or layers of the particular film unit in such a manner that it is stable, non-migratory or non-diffusible, and yet available when required in the development process.

The art accordingly contains several references to "hydrolyzable" photographic reagent precursors. For example, U.S. Pat. No. 3,265,498 issued Aug. 9, 1966 discloses hydrolyzable development restrainer precursors, including those containing a mercapto-azole or mercapto-azine moiety. However, prior to the present invention, the novel quinone- and naphthoquinone-methide precursors of the present invention have been unknown in the art. Several commonly assigned copending applications and U.S. Patents disclose photographic uses for the class of novel quionone- or naphthoquinone methide hydrolyzable precursors of this invention. Copending application Ser. No. 349,063, filed Apr. 9, 1973 in the name of Stanley M. Bloom et al (and its parent application Ser. No. 210,650, filed Dec. 22, 1971 and now abandoned) describes a class of hydropyrimidine compounds within the scope of the present compounds as being useful development restrainers in dye developer diffusion transfer photographic color processes. U.S. Pat. No. 3,785,813, issued Jan. 15, 1974 from application Ser. No. 214,665, filed Jan. 3, 1972, discloses that species of the last-mentioned compounds wherein a ring system of one or more rings is fused to the hydropyrimidine nucleus exhibit significantly greater photographic activity, i.e., development restraint, in such diffusion transfer photographic color processes. Copending application Ser. No. 402,130, filed Oct. 1, 1973 as a continuation-in-part of the aforementioned application Ser. No. 214,665 claims the aforementioned polycyclic hydropyimidine compounds and precursors per se. U.S. Pat. No. 3,756,825, issued Sept. 4, discloses the use of said polycyclic hydropyimidine compounds as toners in black-and-white silver diffusion transfer processes. Our U.S. Pat. No. 3,674,478 issued July 4, 1972 describes integral positive-negative diffusion transfer products and processes employing novel compounds within the scope of this invention.

SUMMARY OF THE INVENTION

Novel compounds are provided in accordance with this invention which release a mercapto-azole or mercapto-azine photographic reagent in the presence of alkali. Since these novel compounds split off a quinone-methide or naphthoquinone methide compound in alkali, they may be defined generically as quinone-methide or naphthoquinone-methide precursors containing a mercapto-azole or mercapto-azine moiety. They may also be defined as phenols or naphthols (including protected derivatives thereof) having a mercapto-azole or mercapto-azine moiety bonded to a nuclear carbon atom in a position ortho or para to the hydroxyl group through a methylene linkage.

The novel compounds of this invention are useful in photographic processes and products wherein it is desirable that a mercapto-substituted azole or azine photographic reagent be made initially unavailable for participation in the photographic process in a non-active, stable form, and yet is made available at some subsequent time in the process, e.g. when contacted by the aqueous alkaline developing medium.

DETAILED DESCRIPTION OF THE INVENTION

The novel compounds of the present invention may be represented by the formula:

A

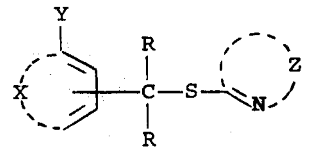

wherein:

X represents the atoms necessary to complete a benzene or naphthalene nucleus, including substituents thereon, if any, e.g. a "ballasting" or "hydrolysis-retarding" substituent;

Y is hydroxyl or protected hydroxyl, i.e. a substituent which upon hydrolysis provides a hydroxyl radical, e.g. acyloxy such as acetoxy, carbethoxy, etc.

Z represents the atoms necessary to complete an azole (5-membered) or azine (6-membered) heterocyclic nucleus, including substituents thereon, if any, e.g. alkyl, aryl, nitro, amino, alkoxy, etc.; and each R represents hydrogen or a lower (1–4 carbon) alkyl group, e.g. methyl, ethyl, etc.
with the

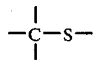

linkage being bonded to a nuclear carbon atom of X in a position ortho or para to the Y substituent.

As indicated, X may include nuclear substituents if desired, for example, to accomplish a specified purpose. As an illustration, X may include an "anchoring" or "ballasting" substituent which renders the compound essentially non-diffusible, i.e. a substituent such as is described in U.S. Pat. No. 3,443,940, e.g., an alkyl group containing at least ten carbon atoms, such as decyl, dodecyl, stearyl, oleyl, etc., linked directly to the aromatic nucleus or indirectly through an appropriate linking group such as a —CONH—, alkylene—CONH— or

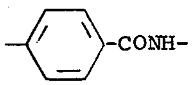

linkage or an aromatic ring, e.g., of the benzene or naphthalene series, or a heterocyclic ring, which rings may be either bonded to a single carbon atom of the aromatic nucleus formed by the X atoms or fused thereto by being bonded to a pair of adjacent carbon atoms; or a polymeric substituent, e.g., a high polymer backbone; or a plurality of short chain radicals which together provide the anchoring moiety.

If desired, the benzene or naphthalene nucleus of the novel compounds of this invention may have other substituents providing particular desired function, e.g., a substituent which will retard or slow down the hydrolysis rate and hence control the rate or time of release of the mercapto reagent in photographic products to be described hereinafter.

Accordingly, X may comprise a group of the formula:

B.

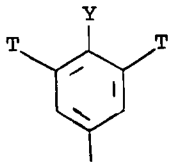

wherein T is hydrogen, alkyl, e.g. lower (1–4 carbon) alkyl such as methyl, propyl, t-butyl, etc., aryl, e.g. phenyl or halide, e.g. chloro; or a group of the formula

C.

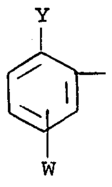

wherein W is hydrogen, alkyl, aryl, halide, nitro, alkoxy, amino, amidoalkyl, carbonyl, carboxyl, sulfo, formyl, etc., or a group of the formula:

D.

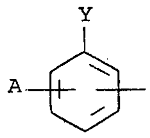

or

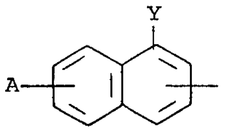

wherein A is hydrogen or an anchoring or ballasting substituent as previously described, e.g. dodecylamidoalkyl or a high polymer backbone. Y in each instance has the definition given previously.

The moiety containing Z may be derived from a wide variety of heterocyclic mercapto compounds heretofore well-known and extensively employed in silver halide photographic processes as photographically active reagents including, for example, image stabilizers, development restrainers or arrestors, anti-foggants, emulsion stabilizers, toning agents, anti-bronzing and anti-plumming agents, and the like. These heterocyclic compounds may be generically represented by the formula:

E.

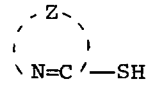

wherein Z is as previously defined.

As is known in the photographic art, Z may include one or more heterocyclic or hydrocarbon rings fused or condensed to the principal 5-membered (azole) or 6-membered (azine) heterocyclic nucleus. Suitable heterocyclic compounds from which the heterocyclic nucleus of Z can be derived include the azoles and azines such as thiazoles (e.g., benzothiazoles), oxazoles (e.g., benzoxazoles), selenazoles (e.g., benzoselenazoles) diazoles (e.g., imidazoles, benzimidazoles, imidazolines, oxadiazoles, thiadiazoles, etc.), triazoles (e.g., 1,2,4-triazoles), pyrimidines, pyrazolopyrimidines, purines, 1,2,4-triazines, s-triazines, tetrazoles, urazoles, oxazolines, thiadiazines, azaindenes (e.g., tetrazaindenes) and the like.

Such photographic stabilizing and fog-inhibiting mercapto-substituted azoles and azines are well known in the art, for example, as indicated by a multiplicity of U.S. Patents directed thereto. Illustrative of U.S. Patents describing such compounds are those classified in Class 96, subclass 109 and related classifications, for example, U.S. Pat. Nos. 3,695,880 (dimercapto-pyrazolopyrimidines); 3,642,473 (mercapto-substituted purines); 3,407,067 (mercapto-oxazoles); 3,407,068 (mercapto-selenazoles); 3,362,826 (mercapto-thiodiazoles and -oxadiazoles); 3,397,987 and 3,335,009 (mercapto heterocyclic nitrogen compounds); 3,330,657 (2,5-dimercapto-1,3,4-thiadiazoles); 3,224,521 (mercapto-pyrazolopyrimidines); 3,244,522 (mercapto-benzenes and -xylenes); 3,418,982 and 3,160,505 (4-mercapto-imidazolidines); 3,051,570 (mercapto-1,2,4-thiadiazoles); 3,008,829 (dithiocatechols, dithio-resorcinols, dithiohydroquinones); 2,956,876 (mercapto-tetrazaindenyls and -pentazaindenyls); 3,692,527 (2-mercapto-4-keto-3,4-dihydropyrimidines); 2,824,001 (mercapto-aminocarbalkoxythiazoles); 3,252,799 (mercapto-imidazoles); 3,637,393 (mercapto-tetrazoles); 3,650,760 (alkoxy mercapto phenols); 3,203,800 (mercapto butyric acid anilides); 3,785,813 and 3,756,825 (mercapto-substituted hydropyrimidines); etc.

As further examples of suitable mercapto compounds, mention may be made of the various toning agents, such as 2-thio-6-amino-uracil, 4-hydroxy-2-mercapto-6-methyl primidine, 5,6-dimethyl-4-hydroxy-2-mercapto-pyrimidine, 4-hydroxy-2-mercapto-6-phenyl pyrimidine, 2-mercaptoorotic acid, 2-mercapto-4-methyl-pyrimidine, 4,6-dimethyl-2-mercapto pyrimidine, 2,5-dimercapto-1,3,4-thiadiazole, 5-mercapto-3-phenyl-1,3,4-thiadiazole-2-thione potassium salt, 2-thio uracil-5-carboxylic acid, 5-ethyl-2-thiobarbituric acid, 2-mercapto-1-methylimidazole, 2-mercapto-3-phenyl-4,6,6-trimethyl dihydro pyrimindine, -mercaptoacetanilide, o-mercapto benzoic acid, cysteine, 2-mercapto-benzoxazole, 2-mercapto-6-nitrobenzothiazole, 2,3-quinoxaline dithiol, mercaptopropionic acid sodium salt, thiobarbituric acid, thiouracil, mercaptosuccinic acid, toluene 3,4-dithiol, 4-amino-2-thiouracil, 2-aminothiophenol, 2-(mercaptomethyl)-pyridine, 2-acetamido-5-mercapto-1,3,4-thiodiazole, 4-aza-2-mercaptobenzimidazole, 6-amino-8-mercaptopurine, 2-amino-6-hydroxy-8-mercaptopurine, 2-(furfurylamino) ethanethiol, 2-(a,a-methylphenethylamino) ethanethiol, rhodanine, 2-(3-diethylaminopropylamino) ethanethiol, 2-cyclohexylaminoethanethiol, dodecanethiol, etc.; antifoggants including many of the above-mentioned toning agents as well as others such as mercaptoimidazoles, e.g., 1-methyl-2-mercapto-4,5-diphenylimidazole, 1,4,5-triphenyl-2-mercaptoimidazole, 1-phenyl-2-mercapto-4,5-difurylimidazole, 1-ethyl-2-mercapto-4,5,-diphenylimidazole, 1-methyl-2-mercapto-4,5-difurylimidazole, 1-phenyl-2-mercapto-4,5-di(p-methylphenyl)-imidazole, 1-phenyl-2-mercapto-4,5-di-(p-chlorophenyl)-imidazole, 1,5-diphenyl-2-mercapto-4-furyl-imidazole, etc.; a mercaptotetrazaindene such as 5-ethoxycarbonyl-2-thio-6-oxo-1,3,3a,7-tetrazaindene; oxadiazoles such as 2-mercapto-5-phenyl-1,3,4-oxadiazole, 2-mercapto-5-(m-nitrophenyl)-1,3,oxadiazole, 2-mercapto-5-(p-nitrophenyl)-1,3,4-oxadiazole, 2-mercapto-5-(p-methoxyphenyl)-1,3,4-oxadiazole, etc.; mercaptothiazoles such as 5-amino-4-carbethoxy-2-mercaptothiazole, 5-methylamine-4-carbethoxy-2-mercaptothiazole, 5-amino-4-carbamyl-2-mercaptothiazole, and various other known antifoggants such as the thiazoles, pyrimidines, benzimidazoles, triazoles, tetrazoles, thioanilides, etc. too numerous to mention.

As illustrated by a number of the above-cited exemplary compounds and as known in the art, the organic mercapto photographic reagents from which the Z moiety is derived, i.e. the compounds of formula E may be unsubstituted or may include substituents on the various nuclei and/or carbon chains comprising Z. Accordingly, Z may include any of the substitutents common for such photographic mercapto compounds such as, for example, hydrocarbon substituents including alkyl and aryl radicals, and nonhydrocarbon substituents including alkoxy, phenoxy, carboxy, carbalkoxy, carboxyalkyl, carboxyphenyl, carboxylate, halogen, cyano, nitro, amino, substituted amino, sulfo, sulfamyl, substituted sulfamyl, sulfonylphenyl, sulfonylalkyl, fluosulfonyl, sulfonamidophenyl, sulfonamidoalkyl and other well-known substituents too numerous to mention herein. As previously mentioned, the selection of the various possible substituents is not a critical feature of the claimed novel compounds and is considered well within the skill and knowledge of the artisan practicing the invention.

Especially useful compounds are derivatives of the so-called "development restrainers" wherein Z represents the atoms necessary to complete a nucleus of the azole series, e.g. the 1-phenyl-5-mercaptotetrazole series, which may include any of the substituents just described.

As specific examples of hydrolyzable precursors of 1-phenyl-5-mercapto-tetrazole series within the scope of this invention, mention may be made of the following:

1.

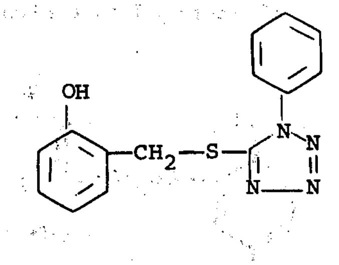

1-phenyl-5-(o-hydroxybenzylthio)-tetrazole

2.

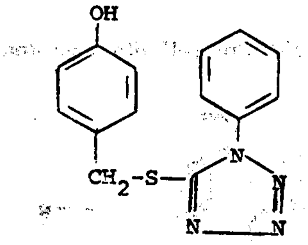

1-phenyl-5-(p-hydroxybenzylthio)-tetrazole

3.

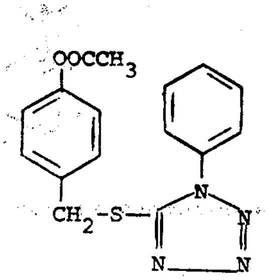

1-phenyl-5-(p-acetoxybenzylthio)-tetrazole

4.

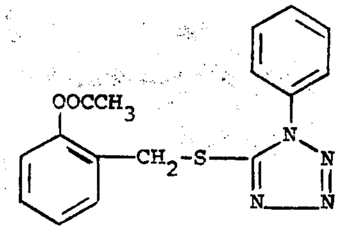

1-phenyl-5-(o-acetoxybenzylthio-tetrazole

5.

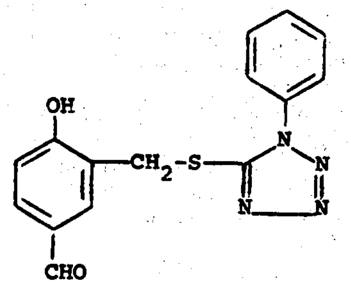

1-phenyl-5-(2'-hydroxy-5'-formyl-benzylthio)-tetrazole

6.

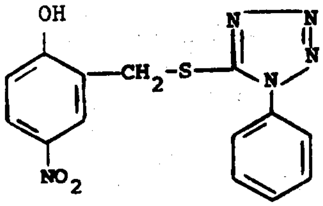

1-phenyl-5-(2'-hydroxy-4'-nitrobenzylthio)-tetrazole

7.

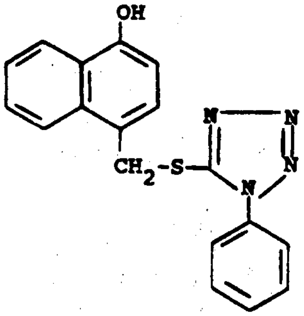

1-phenyl-5-(4'-hydroxy-naphthylmethylthio)-tetrazole

8.

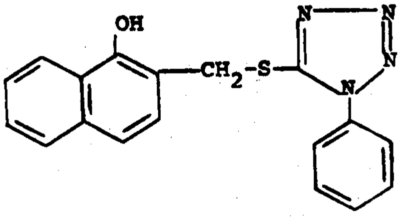

1-phenyl-5-(2'-hydroxy-naphthylmethylthio)-tetrazole

9.

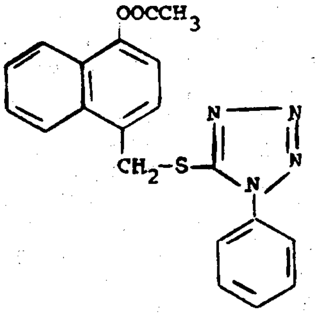

1-phenyl-5-(4'-acetoxy-naphthylmethylthio)-tetrazole

10.

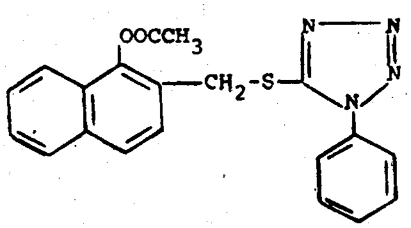

1-phenyl-5-(2'-acetoxy-naphthylmethylthio)-tetrazole

11.

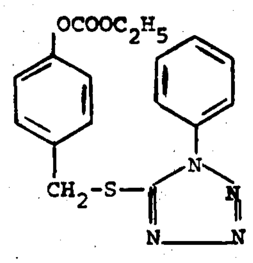

1-phenyl-5-(p-cathyloxybenzylthio)-tetrazole

12.

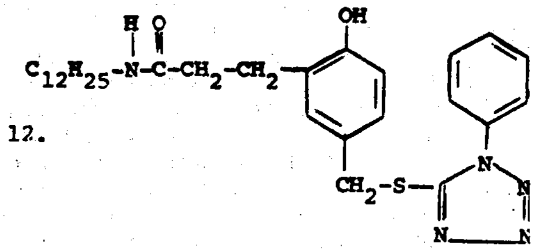

1-phenyl-5-(4'-hydroxy-3'-dodecylamidoethylbenzylthio)-tetrazole

13.

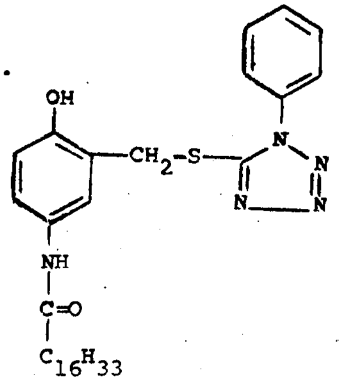

1-phenyl-5-(2'-hydroxy-5'-hexadecylamidobenzylthio)-tetrazole

14.

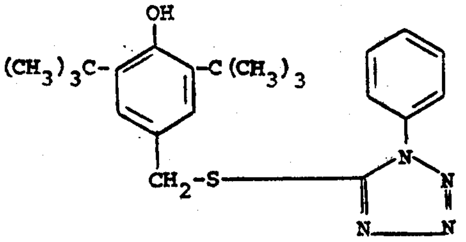

1-phenyl-5-[4'-hydroxy-3', 5'-di(t-butyl)-benzylthio]-tetrazole

15.

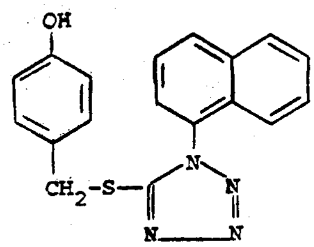

1-naphthyl-5-(p-hydroxy-benzylthio)-tetrazole

16.

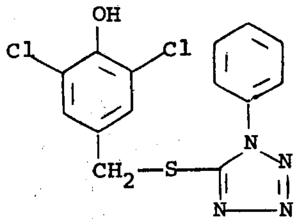

1-phenyl-5-(4'-hydroxy-3', 5'-dichlorobenzylthio)-tetrazole

As further illustrative examples of compounds within the scope of formula A, mention may be made of compounds represented by the following formulae:

17.

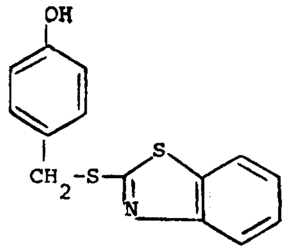

18.

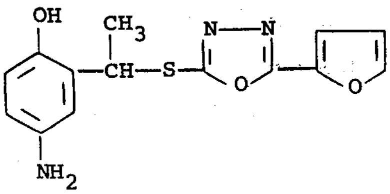

19.

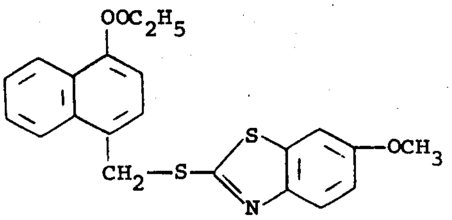

20.
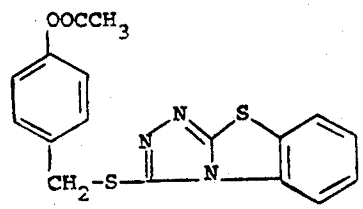
21.
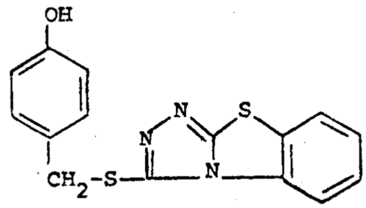
22.
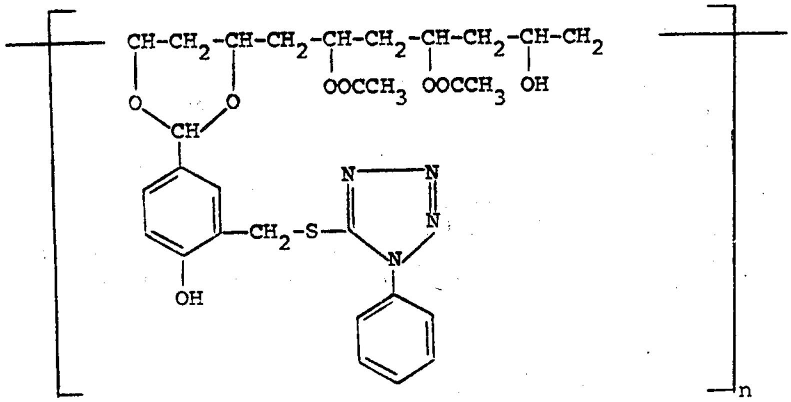
23.
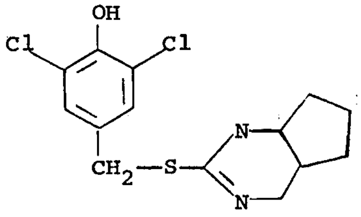
24.
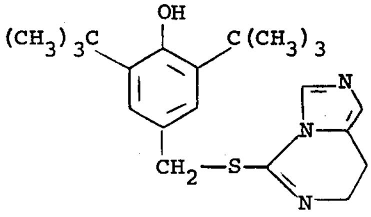
25.
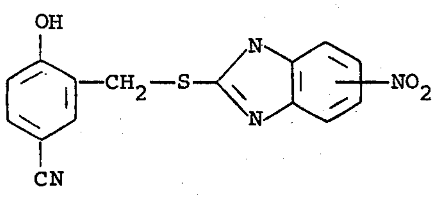

26.

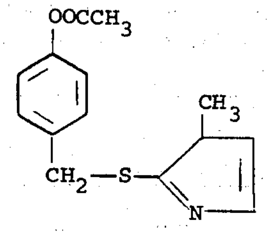

27.

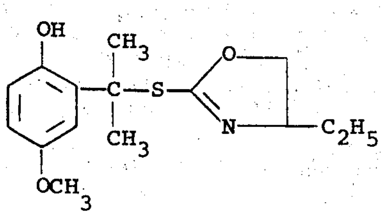

In general, the novel compounds of this invention are readily obtainable by appropriate known replacement or substitution reactions. In such reactions it may be, and usually is desirable to protect the phenolic hydroxyl group during the reaction step by which the photographic mercapto-azole or azine moiety is incorporated.

By way of illustration, photographic reagents containing a mercapto group, e.g. those represented by formula E are readily incorporated by reaction with a protected chloromethyl phenol or naphthol, e.g., ortho- or para-acetoxy-benzyl chloride:

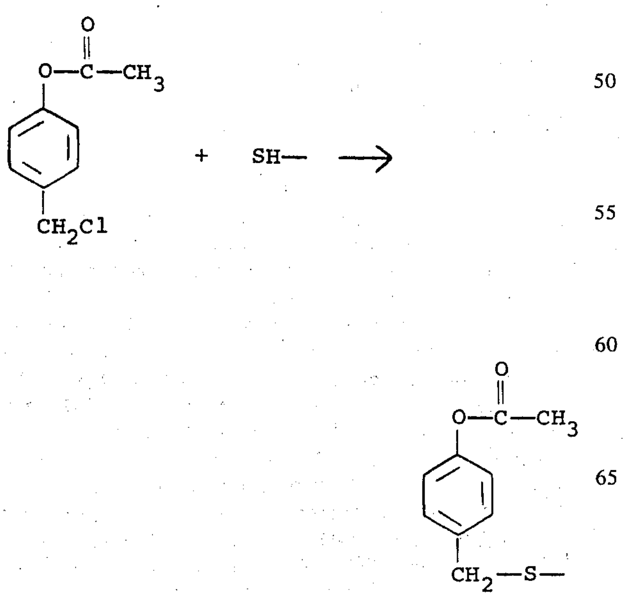

followed by hydrolysis in acid:

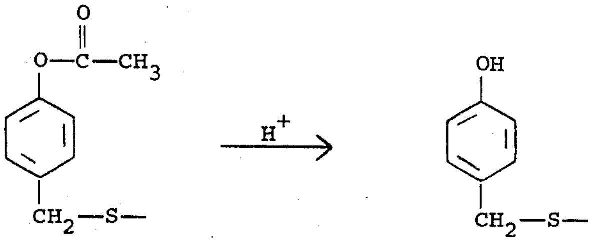

Further by way of illustration, the following reactions illustrate the preparation of a compound of this invention containing a developer restrainer, 1-phenyl-5-mercaptotetrazole, as the mercapto-substituted compound providing the Z moiety:

[1]

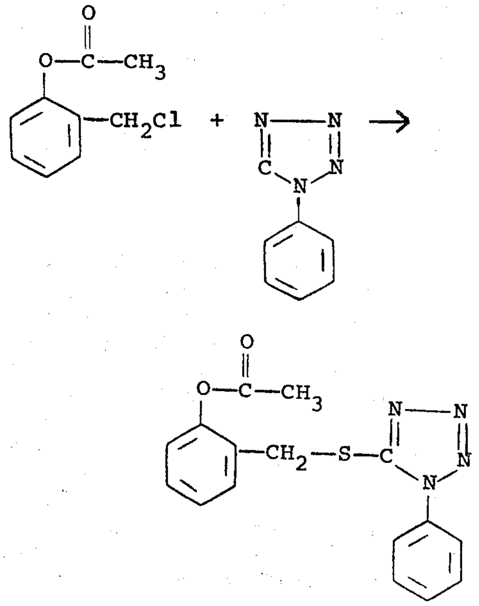

The following examples show by way of illustration and not by way of limitation the preparation of the novel compounds of this invention.

EXAMPLE 1

15 g. of o-hydroxybenzyl alcohol were gradually added while stirring to 45 g. of ice-cooled acetyl chloride. About 30 minutes after the addition had been completed, unchanged acetyl chloride was evaporated using a thin film evaporator. 50 ml. of water were then added to the residue followed by neutralization by adding solid sodium bicarbonate. This mixture was extracted three times with 50 ml. of ethyl ether (each extraction) and the ether phase was then dried. Vacuum distillation yielded 17 g. of o-acetoxybenzyl chloride, a colorless liquid, b.p. (1.5 mm) 98°–102° C.

EXAMPLE 2

100 g. of p-hydroxybenzyl alcohol were added in small portions, while stirring, to 300 ml. of ice-cooled acetyl chloride. Upon standing at room temperature overnight, the major portion of excessive acetyl chloride had evaporated and the remainder was removed using a thin film evaporator. The residue was then neutralized by shaking with concentrated aqueous sodium bicarbonate solution. The aqueous phase was extracted twice with 100 ml. of ethyl ether and the combined organic layers were filtered and then dried. Vacuum distillation yielded 81 g. of pure p-acetoxybenzyl chloride, a colorless liquid, b.p. (1.5 mm) 104°–106° C.

EXAMPLE 3

45 g. of the sodium salt of phenylmercaptotetrazole were dissolved in 500 ml. of acetone. This solution was then filtered and heated to boiling, after which a solution of 41.5 g. of o-acetoxybenzyl chloride (as prepared in Example 1) in 100 ml. of acetone were added. The resulting solution was refluxed for 2 hours and filtered. The filtrate was evaporated to yield a solid residue which was extracted with warm 3% aqueous sodium bicarbonate solution. After filtration the solid material was washed with water and then dried to yield 64.5 g. of 1-phenyl-5-(o-acetoxybenzylthio)-tetrazole (formula 4), white crystals melting at 103°–105° C.

| Elemental Analysis: | C | H | N | S |
|---|---|---|---|---|
| Calculated: | 59.0 | 4.3 | 17.2 | 9.8 |
| Found: | 58.8 | 4.6 | 16.9 | 9.7 |

64.5 g. of the compound of formula 4 (as prepared above) was dissolved in 1.6 l. of methanol, 15 ml. of 10% aqueous hydrochloric acid were added and the solution was then heated while stirring to 55°–57° C in the presence of nitrogen. After 2 hours 100 ml. of methanol were slowly added to replace methanol which had evaporated. After two more hours the methanol was flushed off using a thin film evaporator. The solid residue was pulverized, extracted with warm dilute aqueous sodium bicarbonate solution, washed with water and then dried. Recrystallization from benzene/hexane yielded 46 g. of 1-phenyl-5-(o-hydroxybenzylthio)-tetrazole (the compound of formula 1), white crystals melting at about 102° C, soluble in methanol and benzene and slightly soluble in water.

| Elemental Analysis: | | | | |
|---|---|---|---|---|
| Calculated: | 59.2 | 4.2 | 19.7 | 11.8 |
| Found: | 59.3 | 4.3 | 19.5 | 11.6 |

EXAMPLE 4

45 g. of the sodium salt of phenylmercaptotetrazole were dissolved in 500 ml. of acetone. This solution was filtered and heated to boiling, after which 41.5 g. of p-acetoxybenzyl chloride (as prepared in Example 2) in 100 ml. of acetone were added. The resulting solution was refluxed for 2 hours and filtered. The filtrate was evaporated to yield a solid residue which was extracted with warm 3% aqueous sodium bicarbonate solution. It was then filtered and the solid material recovered was washed with water and dried in a vacuum over to yield 72 g. of 1-phenyl-5-(p-acetoxybenzylthio)-tetrazole (the compound of formula 3), white crystals melting at 71°–72° C.

| Elemental Analysis: | C | H | N |
|---|---|---|---|
| Calculated: | 59.0 | 4.3 | 17.2 |
| Found: | 58.9 | 4.3 | 17.3 |

57 g. of the last-mentioned compound were dissolved in 1.3 l. of methanol. 10 ml. of 10% aqueous hydrochloric acid were added and the solution was heated to 55°–57° C while stirring and in the presence of nitrogen. After 2 hours 100 ml. of methanol were added slowly to replenish evaporated methanol. About 1 hour later the methanol was flashed off using a thin film evaporator. The resulting solid residue was pulverized, extracted with warm dilute sodium bicarbonate solution, washed with water and dried. Recrystallization from benzene/hexane yielded 35 g. of 1-phenyl-5-(p-hydroxybenzylthio)-tetrazole, (the compound of formula 2) white crystals melting at 130°–131° C, soluble in methanol and benzene and slightly soluble in water.

| Elemental Analysis: | | | | |
|---|---|---|---|---|
| Calculated: | 59.2 | 4.2 | 19.7 | 11.8 |
| Found: | 59.2 | 4.4 | 19.7 | 11.3 |

The novel compounds of this invention are useful in the field of photography, and particularly in photographic products wherein it is desirable that a mercapto-azole or mercapto-azine photographic reagent be contained in a layer or layers of a film unit in a stable, non-migratory or non-diffusible, inactive form, yet can be made available in active form when required in the photographic process. The use of these compounds is considered generally advantageous in photographic processes wherein a photosensitive element comprising a support carrying a light-sensitive silver halide layer is employed to form silver or dye images.

One such use for the novel compounds of this invention is fully and adequately described in our aforementioned U.S. Pat. No. 3,674,478, issued July 4, 1972, including comparative photographic data with prior art photographic reagents (e.g. see Examples 6–13 set forth therein) and therefore need not be described in great detail herein. U.S. Pat. No. 3,674,478 is incorporated by reference herein in its entirety to describe in detail a preferred utility for the present novel compounds.

Said patent describes photographic film units for forming diffusion transfer images in color wherein a quinone- or naphthoquinone-methide precursor containing a mercapto-substituted development restrainer in accordance with the present invention is disposed in a layer of the film unit. In general, the film units of the foregoing description are exposed to form a developable image and thereafter developed by applying the appropriate alkaline processing composition to develop exposed silver halide and to form, as a function of development an imagewise distribution of diffusible dye image-providing material which is transferred, at least in part, by diffusion, to a dyeable stratum to impart thereto the desired color transfer image, e.g. a positive multicolor dye image. When this alkaline processing composition contacts the precursor compound in its location in the film unit, the precursor compound decomposes and splits off the active form of the development restrainer, which is then free to diffuse to the silver halide and retard or arrest further development thereof. For a more exact description of this particular embodiment, reference should be made to the aforementioned incorporated patent.

It should be understood that the present compounds are not limited in their usefulness to any particular photographic system. For any of the known systems for forming positive and/or negative silver or dye images, it is commonly desirable to employ photographic reagents performing desired functions, e.g. toning agents to achieve a silver image having more of a blue-black tonal quality, anti-foggants and the like to prevent chemical and/or physical fog, etc. and the compounds of the present invention provide an advantageous means for incorporating these reagents in the photographic product.

Where found desirable or expedient to do so, the compounds of this invention may be employed in the film units in their protected form which upon contact with an aqueous alkaline medium hydrolyze to form the corresponding phenol. Incorporation in this manner may provide a means or retarding release of the photographic reagent where such retardation is desired, particularly where the protected group is not rapidly removable by hydrolysis.

In instances wherein it is desired further to immobilize the compound or the benzyl alcohol ultimately obtained from the quinone-methide formed upon release of the photographic reagent, the above-noted anchoring substituent may be included in the compound.

For a more complete understanding of the photographic employment of the novel compounds of this invention, reference is made to the following examples which are intended to be illustrative of one use for said compound and are not to be interpreted as limiting in any way.

EXAMPLE 4

On a transparent polyethylene terephthalate film base was coated a 7:3 mixture, by weight, of polyethylene/maleic acid copolymer and polyvinyl alcohol at a coverage of about 1,000 mgs./ft.$^2$ to provide a polymeric acid layer. Over this was coated a graft copolymer of acrylamide and diacetone acrylamide on a polyvinyl alcohol backbone in a molar ratio of 1:3.2:1 at a coverage of about 750 mgs./ft.$^2$ to provide a polymeric spacer or timing layer. A layer was next applied comprising a mixture of the aforementioned graft copolymer and a compound of formula 2 at a coverage of 750 mgs./ft.$^2$ of graft copolymer and 72 mgs./ft.$^2$ of the compound of formula 2. Finally, a dyeable stratum comprising a 2:1 mixture by weight of polyvinyl alcohol and poly-4-vinylpydine was coated at a coverage of about 500 mgs./ft.$^2$ to provide the positive component of an integral negative-positive film unit.

To prepare an integral negative-positive film unit, the positive component prepared in Example 4 is placed in superposition with the negative component and the respective components are then laminated or otherwise maintained together to provide the requisite film unit. If desired it may be taped together in laminate form, at their respective edges, by means of a pressure-sensitive binding tape extending around, in contact with, and over the edges of the resulting laminate.

The following example illustrates a typical negative component which may be employed in combination with the aforementioned positive component to provide a composite film unit.

EXAMPLE 5

The negative component may be prepared by coating in succession, on an opaque film base the following layers:

1. A layer of cyan dye developer dispersed in gelatin and coated at a coverage of about 80 mgs./ft.$^2$ of dye and about 100 mgs./ft.$^2$ of gelatin;
2. A red-sensitive gelatino-silver iodobromide emulsion coated at a coverage of about 225 mgs./ft.$^2$ of silver and about 50 mgs./ft.$^2$ of gelatin;
3. A layer of acrylic latex sold by Rohm and Haas Co. under the trade designation AC-61 and polyacrylamide coated with a coverage of about 100 mgs./ft.$^2$ of AC-61 and about 5 mgs./ft.$^2$ of polyacrylamide;
4. A layer of magenta dye developer dispersed in gelatin and coated at a coverage of 70 mgs./ft.$^2$ of dye and about 120 mgs./ft.$^2$ of gelatin;
5. A green-sensitive gelatino-silver iodobromide emulsion coated in a coverage of about 120 mgs./ft.$^2$ of silver and 60 mgs./ft.$^2$ of gelatin;
6. A layer comprising the acrylic latex sold by Rohm and Haas Co. under the trade designation B-15 and polyacrylamide coated in a coverage of about 100 mgs./ft.$^2$ of B-15 and about 10 mgs./ft.$^2$ of polyacrylamide;
7. A layer of a yellow dye developer and the auxiliary developer 4'-methylphenyl hydroquinone dispersed in gelatin and coated at a coverage of about 50 mgs./ft.$^2$ of dye, about 15 mgs./ft.$^2$ of auxiliary developer and 50 mgs./ft.$^2$ of gelatin;
8. A blue-sensitive gelatino-silver iodobromide emulsion coated at a coverage of about 75 mgs./ft.$^2$ of gelatin; and
9. A layer of gelatin coated at a coverage of about 50 mgs./ft.$^2$ of gelatin.

The three dye developers employed above may be the following:

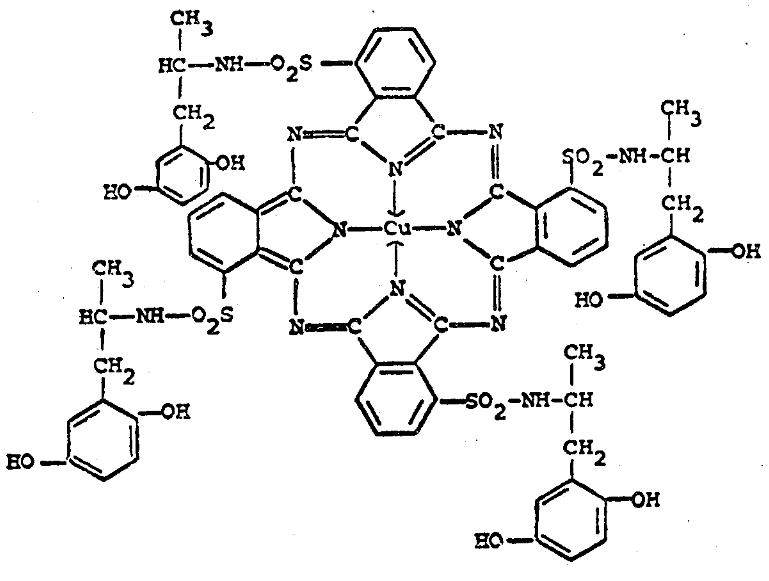

a cyan dye developer;

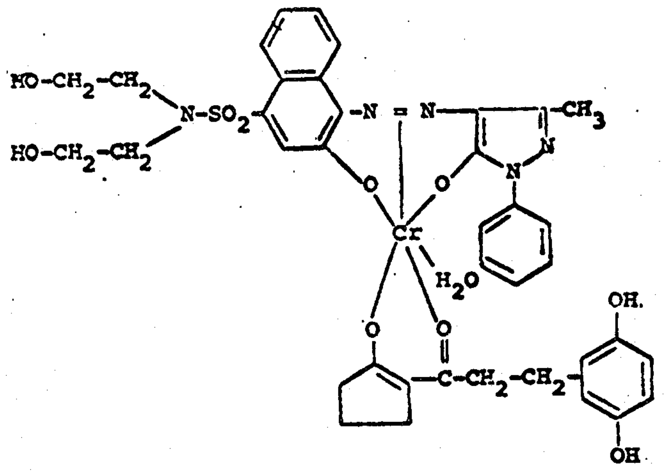

a magenta dye developer; and

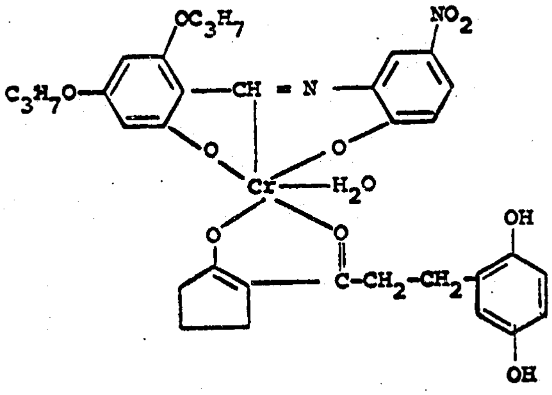

a yellow dye developer.

Film units containing the positive component of this invention were compared with control film units containing a conventional development restrainer, 1-phenyl-5-mercaptotetrazole (PMT) in the dyeable stratum or in an underlying layer, i.e., a structure analogous to that described in Example 4.

The following examples show the preparation of these control components.

EXAMPLE 6

On a transparent polyethylene terephthalate film base was coated the polymeric acid layer referred to in Example 4 at the same coverage, i.e., 1,000 mgs./ft.$^2$. Over this was applied the graft copolymer referred to in Example 4 at the same coverage, i.e., 750 mgs./ft.$^2$. Finally, a mixture comprising a 2:1 mixture by weight of polyvinyl alcohol and poly-4-vinylpyridine was coated at a coverage of about 735 mgs./ft.$^2$ of this mixture and 15 mgs./ft$^2$ of PMT to provide a positive component wherein the development restrainer (PMT) was contained in the dyeable stratum.

EXAMPLE 7

On a transparent polyethylene terephthalate film base was coated the polymeric acid layer referred to in Example 4 at the same coverage, i.e., 1,000 mgs./ft.$^2$. Over this was applied a layer of the graft copolymer referred to in Example 4 at a coverage of 750 mgs./ft.$^2$. A layer was next applied comprising a mixture of this graft copolymer and PMT at a coverage of about 750 mgs./ft.$^2$ of the graft copolymer and 45 mgs./ft$^2$ of PMT. Finally, the dyeable stratum referred to in Example 4 was coated at a coverage of about 500 mgs./ft.$^2$ to provide a positive component wherein the development restrainer is positioned in a layer beneath the dyeable stratum, i.e., a positive component analogous in structure to that prepared in Example 4.

An integral negative-positive film unit prepared by laminating the positive component as prepared in Example 4 to a negative component of the type prepared in Example 5 was compared for contamination with similar control units similar in all respects except that the positive components of the controls were those prepared in Examples 6 and 7. In each instance, exposure times, development procedures, etc., were the same to establish accepted test procedures. One set of tests compared the $D_{min}$ and $D_{max}$ obtained on storage at room temperature for three days. Since the problem of contamination is greater at higher temperatures and/or humidities, another standard-type test compared the $D_{min}$ and $D_{max}$ obtained after storage for 5 days at 100° F and 80% relative humidity.

In each instance, after storage, the film unit was exposed for the same time and then developed by applying between the dyeable stratum and the adjacent layer of the negative component a processing composition comprising the following proportions of ingredients:

| | | |
|---|---|---|
| Water | 100.0 | cc. |
| Titanium dioxide | 50.0 | gms. |
| Carboxymethyl cellulose | 3.4 | gms. |
| Potassium hydroxide | 11.2 | gms. |
| Benzotriazole | 1.7 | gms. |
| 5-hydroxy-4-azabenzimidazole | 0.35 | gm. |
| Phenethyl-a-picolinium bromide | 1.37 | gms. |

The density readings for cyan, magenta and yellow dye transfer were then determined to be as follows:

| | | 3 days at Room Temp. | | 5 days at 100° F and 80% R.H. | |
|---|---|---|---|---|---|
| | | $D_{min}$. | $D_{max}$. | $D_{min}$. | $D_{max}$. |
| Control with | C | .17 | 1.95 | .20 | 2.11 |
| PMT in Dyeable | M | .33 | 1.86 | .41 | 1.91 |
| Stratum | Y | .71 | 1.98 | .95 | 1.75 |
| Control with PMT | C | .18 | 2.46 | .19 | 2.13 |
| in layer under | M | .38 | 2.49 | .42 | 2.27 |
| Dyeable Stratum | Y | .58 | 2.48 | .75 | 2.27 |
| Film Unit with | C | .16 | 2.50 | .18 | 2.27 |
| Formula 2 under | M | .34 | 2.50 | .38 | 2.33 |
| Dyeable Stratum | Y | .45 | 2.50 | .67 | 2.37 |

Comparing first the room temperature test with the heat and humidity storage test for any of the film units, it will be seen that the $D_{mins}$ (unwanted dye transfer) are higher in each instance, due to greater contamination whereby development is prematurely restrained, thus permitting dye which would normally be able to develop the respective silver halide emulsions layers and hence be immobilized to instead remain mobile and diffusible and hence transfer. As would be expected, this contamination is most pronounced in the blue-sensitive emulsion layer, the closest one in point of distance to the development restrainer, as is evidenced by the so-called "yellow flooding" resulting in comparatively high unwanted yellow dye transfer. Thus, for example, in the first control wherein the PMT was in the dyeable stratum, the yellow $D_{mins}$ were 0.71 and 0.95, the latter being at the more extreme storage test, as expected. Placing the PMT more distant as in the second control unit wherein it was positioned in an underlying layer afforded some benefits of lower $D_{min}$ with regard to the yellow dye, as noted by the $D_{min}$ readings of 0.58 and 0.75. No lowering of the $D_{mins}$ for the cyan and magenta were noted however, although the $D_{max}$ for each dye was up. The film unit containing the compound of formula 2 showed clearly superior results. The yellow $D_{mins}$ of 0.45 and 0.67 were appreciably better. The respective $D_{max}$ were also improved.

It should be noted, however, that some contamination was still observed with the compound of formula 2, as observed, for example, by the higher $D_{min}$ in the heat-humidity storage test. Accordingly, use of this compound in lieu of standard development restrainers such as PMT does not at present appear to obviate fully the contamination problem. However, this compound is so markedly superior to such standard development restrainers that it is clear that the present invention provides a great improvement in this regard over the prior systems utilizing development restrainers.

While in the preferred embodiments of this aspect of the invention, the reagent is incorporated in the positive component, it may also be incorporated in the negative component. Since incorporation in the negative component places the reagent in closer proximity to the photosensitive strata to which it is intended to function, when incorporated in the negative form it must be so disposed in such a manner that it will not be available to perform its development restraining action too early in the development process, e.g., it should not be able to perform its restraining function before substantially all of the exposed and developable silver halide has been developed. While various physical means in the form of temporary barriers to migration of the released restrainer may be suggested to those skilled in the art, particularly in the light of the foregoing description, it will be seen that the requisite delay in release of the restrainer may be accomplished chemically by employment of the compounds wherein the Y moiety is a substituent which must first hydrolyze to the corresponding hydroxy compound before the second stage wherein the restrainer is released. The rate of release may thus be controlled by selection of the appropriate Y substituent, e.g., esters which hydrolyze more or less rapidly, or by the inclusion in the nucleus of the reagent of a substituent which affects the rate of hydrolysis.

From the foregoing description and illustrative examples, it will be seen that the present invention provides an effective and practical means for incorporating various photographic reagents in photographic film units intended for the preparation of black-and-white or color images. The photographic reagents so incorporated are generally characterized as being stable and immobile or nondiffusible but yet available to perform their intended function at the requisite time in the development process, e.g., upon hydrolysis by application of an aqueous alkaline medium. The rate of hydrolysis desired may be regulated in accordance with the conditions required in the particular photographic system employed by selection of the appropriate Y substituent e.g., esters which hydrolyze more or less rapidly, or by the inclusion in the nucleus of the reagent of a substituent which affects the rate of hydrolysis.

From the foregoing description and illustrative examples, it will be seen that the present invention provides an effective and practical means for incorporating various photographic reagents in photographic film units intended for the preparation of black-and-white or color images. The photographic reagents so incorporated are generally characterized as being stable and immobile or nondiffusible but yet available to perform their intended function at the requisite time in the development process, e.g., upon hydrolysis by application of an aqueous alkaline medium. The rate of hydrolysis desired may be regulated in accordance with the conditions required in the particular photographic system employed by selection of the appropriate Y substituent of the reagent, which, as heretofore noted, may be a hydroxyl group, a substituent hydrolyzable relatively rapidly to a hydroxyl group, or a substituent hydrolyzable less rapidly to a hydroxyl group.

Since certain changes may be made in the above product and process without departing from the scope of the invention herein involved, it is intended that all matter contained in the above description shall be interpreted as illustrative and not in a limiting sense.

What is claimed is:

1. A compound of the formula:

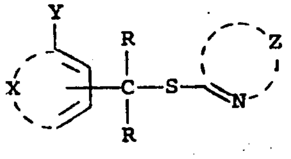

wherein:

X represents the atoms necessary to complete a benzene nucleus, including any alkyl group of at least 10 carbon atoms, phenyl or chloro substituents thereon;

Y is hydroxyl or a protected hydroxyl substituent which upon hydrolysis provides hydroxyl;

Z represents the atoms necessary to complete a 5-(1,2,3,4,-tetrazole) nucleus including a 1-phenyl or 1-naphthyl substituent thereon; and each R represents hydrogen or a 1 to 4 carbon alkyl group, with the — C — S — linkage being bonded to a nuclear carbon atom of X in a position ortho or para to the Y substituent.

2. A compound as defined in claim 1 wherein Y is acyloxy.

3. 1-phenyl-5-(o-hydroxybenzylthio)-tetrazole.

4. 1-phenyl-5-(p-hydroxybenzylthio)-tetrazole.

5. 1-phenyl-5-(p-acetoxybenzylthio)-tetrazole.

6. 1-phenyl-5-(o-acetoxybenzylthio)-tetrazole.

7. 1-naphthyl-5-(p-hydroxybenzylthio)-tetrazole.

8. 1-phenyl-5-(4'-hydroxy-3',5'-di(t-butyl)-benzylthio)-tetrazole.

9. 1-phenyl-5-(4'-hydroxy-3',5'-dichlorobenzylthio)-tetrazole.

* * * * *